United States Patent [19]

Scholz et al.

[11] Patent Number: 5,603,691
[45] Date of Patent: Feb. 18, 1997

[54] METHOD OF USING WATER SOLUBLE FILMS IN CURABLE CASTING TAPES

[75] Inventors: Matthew T. Scholz, Woodbury; Mark A. Berman, St. Paul; Dennis C. Bartizal, Lakeland; Michael D. Delmore, Mounds View, all of Minn.

[73] Assignee: Minnesota Mining and Manufacturing Company, St. Paul, Minn.

[21] Appl. No.: 48,738

[22] Filed: Apr. 16, 1993

[51] Int. Cl.$^6$ ............................................. A61F 5/04
[52] U.S. Cl. ............................................. 602/8; 602/1
[58] Field of Search ................................ 602/1, 2, 3, 8

[56] References Cited

U.S. PATENT DOCUMENTS

| | | | |
|---|---|---|---|
| 3,630,194 | 12/1971 | Boardman | 128/90 |
| 3,908,644 | 9/1975 | Neinart et al. | 128/90 |
| 3,932,526 | 1/1976 | Koshar | 260/607 A |
| 3,972,323 | 8/1976 | Boricheski | 128/91 R |
| 4,131,114 | 12/1978 | Kirkpatrick et al. | 128/90 |
| 4,411,262 | 10/1983 | von Bonin et al. | 128/90 |
| 4,441,262 | 4/1984 | Gazzoni | 34/57 D |
| 4,454,873 | 6/1984 | Laufenberg et al. | 128/90 |
| 4,473,671 | 9/1984 | Green | 523/105 |
| 4,498,467 | 2/1985 | Kirkpatrick et al. | 128/90 |
| 4,502,479 | 3/1985 | Garwood et al. | 128/90 |
| 4,609,578 | 9/1986 | Reed | 428/76 |
| 4,667,661 | 5/1987 | Scholz et al. | 128/90 |
| 4,668,563 | 5/1987 | Buese et al. | 428/230 |
| 4,672,956 | 6/1987 | Potter et al. | 128/90 |
| 4,705,840 | 11/1987 | Buckanin | 528/53 |
| 4,841,958 | 6/1989 | Ersfeld et al. | 128/90 |
| 4,940,047 | 7/1990 | Richter et al. | 128/90 |
| 4,947,839 | 8/1990 | Clark et al. | 602/8 |
| 4,984,566 | 1/1991 | Sekime et al. | 128/90 |
| 5,014,403 | 5/1991 | Buese | 28/170 |
| 5,052,380 | 10/1991 | Polta | 128/90 |
| 5,250,344 | 10/1993 | Williamson et al. | 602/2 |

FOREIGN PATENT DOCUMENTS

| | | |
|---|---|---|
| 0181138 | 5/1986 | European Pat. Off. . |
| 0352095 | 1/1990 | European Pat. Off. . |
| 0407056 | 1/1991 | European Pat. Off. . |
| 0479269 | 4/1992 | European Pat. Off. . |
| 522824 | 1/1993 | European Pat. Off. ............ 602/1 |
| 2200286 | 8/1988 | United Kingdom . |
| WO90/14060 | 11/1990 | WIPO . |
| WO-A-9304709 | 3/1993 | WIPO . |

OTHER PUBLICATIONS

C. R. Noller, *Chemistry of Organic Compounds*, Ch. 6, pp. 121–122 (1957).
International Search Report for PCT/US94/02093.

*Primary Examiner*—Paul Prebilic
*Attorney, Agent, or Firm*—Gary L. Griswold; Walter N. Kirn; F. Andrew Ubel

[57] ABSTRACT

The present invention provides a method of using novel casting tapes incorporating water soluble liners. The liners of the present invention may be used for a number of purposes including: use as an interlayer film liner in a casting tape article to prevent undesirable resin pooling; use as an interlayer liner to lubricate a casting tape when immersed in water; use in a method of producing a decorative casting tape either by retarding layer-to-layer migration of a colored resin or by transferring a design preprinted on the liner to an adjacent casting tape; use as an interlayer liner in a casting tape article to prevent adhesion between adjacent layers of the article; and use as a release liner to facilitate removal of a roll of casting tape from its package. The liners employed in this invention are rapidly soluble in water and may be provided as a continuous or semi-continuous sheet structure.

19 Claims, 1 Drawing Sheet

1

METHOD OF USING WATER SOLUBLE FILMS IN CURABLE CASTING TAPES

FIELD OF THE INVENTION

This invention relates to a liner material useful in preparing an orthopedic bandage.

BACKGROUND OF THE INVENTION

Many different orthopedic casting materials have been developed for use in the immobilization of broken or otherwise injured body limbs. Some of the first casting materials developed for this purpose involve the use of plaster of Pads bandages consisting of a mesh fabric (e.g., cotton gauze) with plaster incorporated into the openings and onto the surface of the mesh fabric.

Plaster of Paris casts, however, have a number of attendant disadvantages, including a low strength-to-weight ratio, resulting in a finished cast which is very heavy and bulky. Furthermore, plaster of Pads casts typically disintegrate in water, thus making it necessary to avoid bathing, showering, or other activities involving contact with water. In addition, plaster of Pads casts are not air permeable, and thus do not allow for the circulation of air beneath the cast which greatly facilitates the evaporation and removal of moisture trapped between cast and skin. This often leads to skin maceration, irritation, or infection. Such disadvantages, as well as others, stimulated research in the orthopedic casting art for casting materials having improved properties over plaster of Paris.

A significant advancement in the art was achieved when polyisocyanate prepolymers were found to be useful in formulating a resin for orthopedic casting materials, as disclosed, for example, in U.S. Pat. No. 4,502,479 (Garwood et al.) and U.S. Pat. No. 4,441,262 (Von Bonin et al.). U.S. Pat. No. 4,502,479 sets forth an orthopedic casting material comprising a knit fabric which is made from a high modulus fiber (e.g., fiberglass) impregnated with a polyisocyanate prepolymer resin such as polyurethane. Orthopedic casting materials made in accordance with U.S. Pat. No. 4,502,479 provide significant advancement over the plaster of Paris orthopedic casts, including a higher strength-to-weight ratio and greater air permeability. U.S. Pat. No. 4,667,661 (Scholz et al.) discloses a casting tape which further comprises a lubricant. The lubricant serves to provide a casting material which is easy to apply and slippery to mold without the resin sticking to the gloved hands of the applier.

Examples of an orthopedic bandage using a polyester fabric which is not a knitted fabric is disclosed in U.S. Pat. No. 3,972,323 (Boricheski) (comprising plaster of Paris binder) and U.S. Pat. No. 4,841,958 (Ersfeld et al.). However, the polyester fabric backing disclosed in U.S. Pat. No. 4,841,958 causes the cast to have a somewhat lower strength and a lower rigidity than fiberglass casts. As such, these casting materials require more layers of casting tape to achieve a weight bearing orthopedic cast.

Several "roll-form" casting tapes have been disclosed which comprise a fabric impregnated with a curable resin. Examples include materials based on free radical acrylate or acrylamide functional resins which may be cured by a redox reaction upon activation by water (see, e.g., U.S. Pat. No. 4,672,956), and two part systems wherein one component is coated on a tape and a separate reactive component is provided in a separate sealed ampoule (see, e.g., U.S. Pat. No. 4,498,467). However, more commercially successful casting tapes generally include materials based on isocyanate functional polyurethane prepolymers. Common to all these roll-form casting tapes, a viscous liquid resin is impregnated into a fibrous backing material such as a knit, woven, or non-woven material. The backings may be comprised of either natural or synthetic fibers or both. In general, the resin is primarily retained (i.e., "held") by the backing by capillary force. However, in order to ensure adequate layer-to-layer lamination in the applied cast it is often necessary to apply more resin than the backing can actually hold. Furthermore, the resin viscosity is often deliberately low to facilitate coating and handling properties such as the ease by which the roll unwinds and the conformability of the material to the patient's limb. Unfortunately, gravitational forces cause resin migration between layers and toward the bottom of the roll. This migration is often referred to as resin "pooling."

A cast material comprising a filled thermoplastic crystalline solid polyurethane is disclosed in U.S. Pat. No. 4,473,671 (Green). In use, the orthopedic cast material is warmed to a sufficiently high temperature to cause the polymer therein to become soft enough to deform. The orthopedic cast material is molded to conform to the surface shape of the effected portion of the body and then is cooled to room temperature. U.S. Pat. No. 4,454,873 (Laurenberg) discloses an orthopedic cast material comprising a thermoplastic material and a coating of (poly)ethylene oxide. The coating is said to prevent adherence of adjacent convolutions of the cast material when it is molten.

A tubular casting system comprising an integral tubular bulky knitted substrate carrying a hardenable resin and an undercast padding layer is disclosed in International Patent Application No. WO 90/14060 (Blottet al.). A water soluble but resin impervious barrier layer intermediate to the padding and resin beating layers is discussed.

From the foregoing, it will be appreciated that what is needed in the art is an orthopedic casting material which has the moldability of plaster of Paris, the high strength-to-weight and good air permeability of non-plaster of Paris materials, and which is non-sticky during application. In this regard it would be a significant advancement in the art to provide such a combination of advantages without actually using plaster of Paris, thereby avoiding the inherent disadvantages of plaster of Paris outlined herein. It would be a further advancement in the art to provide casting materials which resist resin pooling. Such orthopedic casting materials and methods for preparing the same are disclosed and claimed herein.

RELATED APPLICATIONS

Of related interest are the following U.S. Patent Applications, filed concurrently with this application and by the assignee of this invention: Novel Casting Materials, Ser. No. 08/045,007; Process and Novel Casting Materials, Ser. No. 08/048,891; and Novel Casting Tapes and Resins and Processes Therefor, Ser. No. 08/048,656 which are herein incorporated by reference.

Also of related interest are the following U.S. Patent Applications, filed on Jan. 25, 1993 by the assignee of this invention: Water Curable Resin Compositions Ser. No. 08/008,743; Orthopedic Support Materials and Method—Ser. No. 08/008,678; and Microfiber Fillers for Orthopedic Casting Tapes—Ser. No. 08/008,755 which are herein incorporated by reference.

SUMMARY OF THE INVENTION

The present invention provides novel casting tapes incorporating water soluble "liners". The liners of the present invention may be used for a number of purposes including: use as an interlayer film liner in a casting tape article to prevent undesirable resin "pooling"; use as an interlayer liner which lubricates a casting tape upon immersion in water; use in a method of producing a decorative casting tape either by retarding layer-to-layer migration of a colored resin or by transferring a design preprinted on the liner to an adjacent casting tape; use as an interlayer liner in a casting tape article to prevent adhesion between adjacent layers of the article; and use as a release liner to facilitate removal of a roll of casting tape from its package. Preferred embodiments accomplish a number of these benefits. The liners employed in this invention are rapidly soluble in water and may be provided as a continuous or semi-continuous sheet structure.

BRIEF DESCRIPTION OF THE DRAWINGS

The invention may be more clearly understood by reference to the drawings, wherein:

In FIG. 1 a partially unwound roll of casting tape 1, comprising a casting material 2, and a fugitive water-soluble liner 3 is shown. FIGS. 2 and 3 show a perspective view of a casting tape wherein the casting material 2 is in the form of a sheet which has a fugitive water-soluble liner 3 adjacent to both its major surfaces. FIG. 2 depicts the case where a single sheet of a water-soluble liner 3 is folded over both major surfaces of the casting material 2. FIG. 3 depicts the case where two separate water-soluble liners 3 are positioned one on each side of the casting material 2. The liner or liners 3 may be sealed together, if desired, using a sealing means such as an adhesive or other welding method. Alternatively, the liner may be in the form of a tube enclosing the casting material (not shown). FIG. 4 shows a perspective view of a roll of casting tape 4 which is enclosed in a water-soluble bag 5.

DETAILED DESCRIPTION OF THE INVENTION

Figure 1:
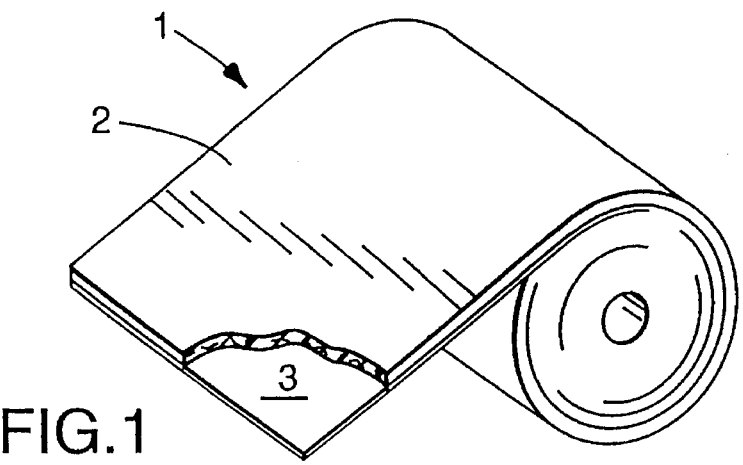
FIG. 1 shows a perspective view of a roll form casting tape comprising a casting material and a water-soluble liner film.
Figure 2:
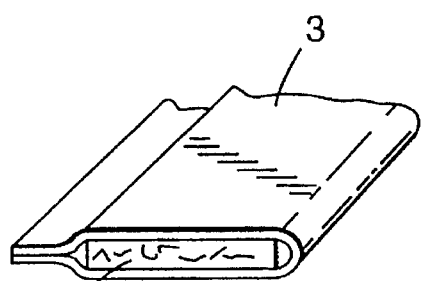
FIGS. 2 and 3 show a perspective view of a casting tape comprising a casting material and a water-soluble liner film.
Figure 3:
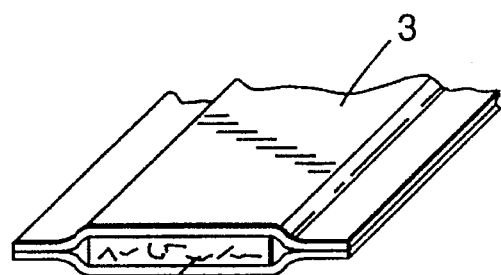
Figure 4:
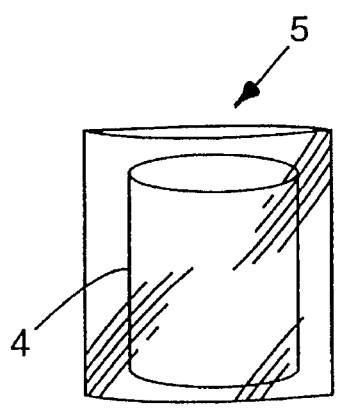
FIG. 4 shows a perspective view of a roll of casting tape in a water soluble bag.

The present invention relates to orthopedic casting materials and methods for preparing and using such orthopedic casting materials, wherein the materials comprise a water-soluble liner, a curable-resin sheet, and optionally a fabric scrim. In particular, the liners employed in the present invention have important characteristics and physical properties which allow the casting materials to possess improved handling characteristics or better distribution of resin (thereby providing a cast with fewer resin deficient regions due to resin pooling) or both. Orthopedic casting materials of the present invention also possess improved lubricity or easier roll unwind or both.

There exists a need for casting products which are slippery during application yet have little or no pooling of resin during storage. Preferably such products optionally have a pleasing and decorative appearance. It has been discovered that casting products which comprise a fugitive water soluble liner possess these desirable properties. Such a liner may be rolled up with the casting tape and stored in a moisture impervious pouch. When present as a film the liner prevents interlayer resin migration and therefore undesirable resin pooling. During use when the roll is immersed or otherwise contacted with water the liner dissolves forming an aqueous polymer solution. The aqueous polymer solution then provides a lubricating effect during application and molding of the cast material. Preferably, the liner is rapidly soluble in water and will effectively dissolve in ambient temperature water in less than 60 seconds, preferably less than 30 seconds and more preferably in less than 10 seconds. By "effectively dissolve" is meant that the liner when mixed with water under the desired conditions of use will solubilize in the water to an extent sufficient to provide a lubricating effect or allow layer-to-layer adhesion of the casting material or both. More preferably the liner when mixed with water under the desired conditions of use dissolves to form a homogeneous liquid mixture.

The materials and compositions of the present invention may be fabricated into a variety of configurations including splints and tapes. When fabricated as a splint, the material may be provided as a precut slab or a continuous length form. When fabricated as a tape, the material preferably comprises a scrim or fibrous material to further enhance the tape's cohesiveness or integrity.

The presently more preferred materials and compositions of the present invention employ a fugitive water soluble web as a liner which separates adjacent layers of the tape (e.g., when the tape is provided as a roll). The incorporation of a "liner" serves several purposes including, for example, providing a prelubricated sheet, retarding resin migration (thereby limiting resin pooling), or providing decorative patterns to the material.

Suitable water soluble liners are comprised of polymers such as polyvinylalcohol ("PVA") and copolymers of PVA (as used herein, the term polyvinylalcohol refers to copolymers derived from, for example, the hydrolysis of polyvinyl acetate, wherein the extent of hydrolysis is preferably greater than 50 percent, more preferably greater than 80 percent), polyacrylamides, polymers incorporating acrylic acid, cellulose ether polymers such as hydroxypropylmethylcellulose, hydroxypropyl cellulose, and hydroxyethylcellulose, polyethyloxazoline, polyethylene oxide (as used herein "polyethylene oxide" and "polyethylene glycol" are synonymous terms), polyethylene oxide and polypropylene oxide random and block-copolymers, esters and urethanes of polyethylene glycol or polyethylene glycol and polypropylene glycol polymers and the like. Copolymer films and laminates and polymer blends are also possible.

Preferably, the liner is rapidly soluble in water and effectively dissolves when exposed to water in less than about 60 seconds (as defined in the examples below), more preferably the liner dissolves when exposed to water in less than 30 seconds and most preferably the liner dissolves when exposed to water in less than 10 seconds. Preferred liners also provide a lubricating effect to the tape when dissolved.

Preferably the liner has sufficient flexibility for processing. Some liner materials (e.g., certain PVAs) may require the incorporation of a plasticizer to achieve a suitable degree of flexibility for use as a liner. Suitable plasticizers may be incorporated into the liner either "internally" or "externally" to the polymer component. An example of a plasticizer which is "internally" incorporated into the liner is a polymer formed by copolymerizing vinyl acetate with polyethylene glycol monomethacrylate (the plasticizer) followed by hydrolysis to PVA and extrusion as a film. An example of a plasticizer which is "externally" incorporated into the liner is the blending of glycols or other small molecules such as esters into a polymer melt. The plasticizer preferably is extremely dry for use with the presently preferred water curable resins. However, for thermoplastic casting materials a low concentration of water may serve as the plasticizer.

Suitable liner films include continuous or non-continuous films. Suitable noncontinuous films include woven or non-woven films such as melt blown PVA films. Being in a non-continuous form such as a non-woven fabric may facilitate dissolution of the liner due to the greatly exposed surface area. Furthermore, porous structures may also provide greater flexibility which may facilitate processing. In use the liner begins dissolving as soon as the product is contacted with water and therefore need not be removed or even perceptible to the clinician. Liners are preferably kept thin to prevent excessive build up of polymer solution which could interfere with layer to layer lamination of the casting tape. Continuous film liners are preferably less than 100 μm thick, more preferably less than 60 μm thick, and most preferably less than 25 μm thick. While the liner itself provides lubrication, an additional lubricant such as disclosed in U.S. Pat. No. 4,667,661 may be added to the composition.

The presently most preferred liner for use with water-curable casting tapes is Aicello Solublon PVA film SA grade 17 micron thick available from Mitsui Plastics Inc. (White Plains, N.Y.). Although, even when dry, this film is potentially reactive with isocyanate functional water-curable resins (since it contains "hydroxyl" functionality) it has been observed that this reaction does not readily occur. It is presently believed that undesirable reactions between such liners and resins can be prevented provided the liner and resin are maintained in a separate "phase" (i.e., the liner should preferably be essentially insoluble in the resin).

For purposes of retarding resin migration the liner is preferably a continuous film and is wound up along with the casting tape such that through the cross section of the roll the layers of casting tape and liner alternate. Alternatively, the liner may be placed on both sides of the casting tape during the winding operation. Furthermore, the liner, if placed on both sides of the casting tape, may be sealed on one or both edges to further prevent resin pooling and migration. In the absence of such a seal, and in order to gain the full benefit of this invention, the roll of casting tape is preferably stored laying on its side rather than on an end. If stored on an end, with an unsealed edge downward, the resin would possibly still pool. Since many casting tapes are currently boxed and stored on their sides this may not be a problem.

It is also possible that certain designs may be produced on the tape by selective coating with colored resins such as those disclosed by U.S. Pat. No. 5,052,380 (Polta). For example, the tape may be produced with a decorative stripe pattern by coating portions of the tape with various colored resins. Alternatively, the tape may be coated with a base color (e.g., a white background) and overcoated by a direct or indirect transfer process with a contrasting colored resin to produce various designs (e.g. polka dots, animals, etc.).

Finally, the water soluble liner of the present invention may also be used to facilitate extraction of a roll of casting tape from its package. For example, the film may be wrapped around the outside of a roll of tape prior to placing it in an aluminum foil laminate pouch, can, or other package. Since the film is preferably non-tacky (as opposed to the resin-impregnated casting tape) it does not stick to the sides of the package thus facilitating removal from the pouch or package. Alternatively, a roll of casting tape may be placed in a bag made from the water soluble liner material. The roll and bag may then be placed in a second traditional pouch and sealed. The inner bag would serve to separate the roll of tape from the inner surface of the outer pouch. When the outer pouch is later opened the roll and inner bag would be easily removed. The inner bag and roll of tape may then be put directly in water to initiate the cure of the resin. There is no need to remove the roll from the inner bag because it simply dissolves away. Alternatively, a strip of water soluble liner material may be wrapped around the circumference of a roll of casting material to prevent the roll from coming unwrapped. When the roll and band are later immersed in water the band dissolves thereby permitting the roll to be unwound. To achieve several benefits of the present invention such as lubricity, easy extraction from the pouch, etc., one may use a non-continuous liner material. For example, a melt blown PVA non-woven sheet may be employed.

The curable-resin used in the casting material of the present invention is preferably any curable-resin which will satisfy the functional requirements of an orthopedic cast. Obviously, the resin or thermoplastic sheet must be nontoxic in the sense that it does not give off significant amounts of toxic vapors during curing or hardening which may be harmful to either the patient or the person applying the cast and also that it does not cause skin irritation either by chemical irritation or the generation of excessive heat during cure. Furthermore, the resin must be sufficiently reactive with the curing agent to insure rapid hardening of the cast once it is applied but not so reactive that it does not allow sufficient working time to apply and shape the cast. Initially, the casting material must be pliable and formable and should adhere to itself. Then in a short time following completion of cast application it should become rigid or at least semi-rigid and strong to support loads and stresses to which the cast is subjected by the activities of the wearer. Thus, the material must undergo a change of state from a liquid or viscous condition to a solid condition in a matter of minutes.

The preferred resins are those cured with water. Presently preferred are urethane resins cured by the reaction of a polyisocyanate and a polyol such as those disclosed in U.S. Pat. No. 4,131,114. A number of classes of water-curable resins known in the art are suitable, including polyurethanes, cyanoacrylate esters, and, when combined with moisture sensitive catalysts, epoxy resins and prepolymers terminated at their ends with trialkoxy- or trihalo-silane groups. For example, U.S. Pat. No. 3,932,526 discloses that 1,1-bis(perfluoromethylsulfonyl)-2-aryl ethylenes cause epoxy resins containing traces of moisture to become polymerized. The following disclosure relates primarily to the presently preferred embodiments of the invention wherein water-curable isocyanate-functional prepolymers, water reactive liquid organometallic compounds, or alkoxy silane terminated polyurethane oligomers are employed as the curable resin.

Resin systems other that those which are water-curable may be used, although the use of water to activate the hardening of an orthopedic casting tape is most convenient, safe and familiar to orthopedic surgeons and medical casting personnel. Resins such as those disclosed in U.S. Pat. No. 3,908,644 in which a bandage is impregnated with difunctional acrylates or methacrylates, such as the bis-methacrylate ester derived from the condensation of glycidyl methacrylate and bisphenol A (4,4'-isopropylidenediphenol) are suitable. The resin is hardened upon wetting with solutions of a tertiary amine and an organic peroxide. Also, the water may contain a catalyst. For example, U.S. Pat. No. 3,630, 194 proposes an orthopedic tape impregnated with acrylamide monomers whose polymerization is initiated by dipping the bandage in an aqueous solution of oxidizing and reducing agents (known in the art as a redox initiator system). The strength, rigidity and rate of hardening of such a bandage is subjected to the factors disclosed herein.

Some presently more preferred resins for use in the present invention are water-curable, isocyanate-functional prepolymers. Suitable systems of this type are disclosed, for example, in U.S. Pat. No. 4,411,262, and in U.S. Pat. No. 4,502,479. Presently more preferred resin systems are disclosed in U.S. Pat. No. 4,667,661 and U.S. patent application Ser. No. 07/376,421 which is herein incorporated by reference. A water-curable isocyanate-functional prepolymer as used herein means a prepolymer derived from a polyisocyanate compound and a reactive hydrogen compound or oligomer (e.g., a "polyol"). As used herein, a reactive hydrogen compound is a compound having active hydrogen in accordance with the well known Zerevitinov test as described, for example, in Chemistry of Organic Compounds by Carl R. Noller, Chapter 6, pp. 121–122 (1957). The prepolymer has sufficient isocyanate-functionality to cure upon exposure to water, e.g., moisture vapor, or preferably liquid water.

It is presently preferred to employ a polyisocyanate prepolymer formed by the reaction of an isocyanate and a polyol. It is preferred to use an isocyanate which has low volatility such as diphenylmethane diisocyanate (MDI) rather than a more volatile material such as toluene diisocyanate (TDI). Suitable isocyanates include 2,4-toluene diisocyanate, 2,6-toluene diisocyanate, mixture of these isomers, 4,4'-diphenylmethane diisocyanate, 2,4'-diphenylmethane diisocyanate, mixture of these isomers together with possible small quantities of 2,2'-diphenylmethane diisocyanate (typical of commercially available diphenylmethane diisocyanate), and aromatic polyisocyanates and their mixture such as are derived from phosgenation of the condensation product of aniline and formaldehyde. Typical polyols for use in the prepolymer system include polypropylene ether glycols (available from Arco Chemical under the trade name Arcol™ PPG and from BASF Wyandotte under the trade name Pluracol™), polytetramethylene ether glycols (Polymeg™ from the Quaker Oats Co. or Terethane™ from the Du Pont de Nemours, E.I., Co., Wilmington, Del.), polycaprolactone diols (Tone™ series of polyols from Union Carbide), and polyester polyols (hydroxyl terminated polyesters obtained from esterification of dicarboxylic acids and diols such as the Rucoflex™ polyols available from Ruco division, Hooker Chemical Co.). By using high molecular weight polyols, the rigidity of the cured resin can be reduced.

An example of a resin useful in the casting material of the invention uses an isocyanate known as Isonate™2143L available from the Dow Chemical Company (a mixture of di- and tri-isocyanates containing about 73% of MDI) and a polypropylene oxide polyol from Union Carbide known as Niax™ PPG725. To prolong the shelf life of the material, it is preferred to include from 0.01 to 1.0 percent by weight of benzoyl chloride or another suitable stabilizer (based on total resin weight).

The reactivity of the resin once it is exposed to the water curing agent can be controlled by the use of a proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using 4-[2-[1-methyl-2-(4-morpholinyl)ethoxy]ethyl]-morpholine (MEMPE) prepared as described in U.S. Pat. No. 4,705,840, the disclosure of which is incorporated by reference, at a concentration of about 0.05 to about 5 percent by weight (based on total resin weight).

Foaming of the resin should be minimized since it reduces the porosity of the cast and its overall strength. Foaming may occur, for example, when carbon dioxide is released as a result of water reacting with an isocyanate group. One way to minimize foaming is to reduce the concentration of isocyanate groups in the prepolymer. However, to have reactivity, workability, and ultimate strength, an adequate concentration of isocyanate groups is necessary. Although foaming is less at low resin contents, adequate resin content is required for desirable cast characteristics such as strength and resistance to peeling. A satisfactory method of minimizing foaming is to add a foam suppressor such as silicone Antifoam A (Dow Corning), or Anti-foam 1400 silicone fluid (Dow Corning) to the resin. It is especially preferred to use a silicone liquid such as Dow Corning Anti-foam 1400 at a concentration of about 0.05 to 1.0 percent by weight. Water-curable resins containing a stable dispersion of hydrophobic polymeric particles, such as disclosed in European Published Patent Application EPO 0 407 056, may also be used to reduce foaming.

An additional lubricant may be added to the resin in accordance with U.S. Pat. No. 4,667,661 such that the casting materials exhibit reduced tack prior to and during cure and yet form a cast with acceptable strength and lamination strength. Suitable lubricants include: hydrophilic groups which are covalently bound to the resin system; additives which are incompatible with the curable resin including: a surfactant, a polymer comprised of a plurality of hydrophilic groups, and a polysiloxane; and combinations of the above. Due to the lubricating effect of the liners of the present invention it is believed that lower concentrations of additional lubricant (than that taught in the 4,667,661 patent) will be needed to provide the desired level of lubrication.

Also included as presently preferred resins in the instant invention are non-isocyanate resins such as water reactive liquid organometallic compounds. These resins are especially preferred as an alternative to isocyanate resin systems. Water-curable resin compositions suitable for use in an orthopedic cast consist of a water-reactive liquid organometallic compound and an organic polymer. The organometallic compound reduces resin viscosity and is a compound of the formula $(R^1O)_xMR^2(y-x)$ wherein: each $R^1$ is independently a $C_1$–$C_{100}$ hydrocarbon group, optionally interrupted in the backbone by 1–50 nonperoxide —O—, —S—, —C(O)—, or —N— groups; each $R^2$ is independently selected from the group consisting of hydrogen and a $C_1$–$C_{100}$ hydrocarbon group, optionally interrupted in the backbone by 1–50 nonperoxide —O—, —S—, —C(O)—, or —N— groups; x is an integer between 1 and y, inclusive; y is the valence of M; and M is boron, aluminum, silicon, or titanium. The organic polymer is either an addition polymer or a condensation polymer. Addition polymers are preferably utilized as the organic polymer constituent. Particularly useful addition polymers are those made from ethylenically unsaturated monomers. Commercially available monomers, from which such addition polymers can be formed, include but are not limited to, ethylene, isobutylene, 1-hexene, chlorotrifluoroethylene, vinylidene chloride, butadiene, isoprene, styrene, vinyl napthalene, ethyl acrylate, 2-ethylhexyl acrylate, tetrahydrofurfuryl acrylate, benzyl acrylate, poly(ethylene oxide) monoacrylate, heptafluorobutyl acrylate, acrylic acid, methyl methacrylate, 2-dimethylaminoethyl methacrylate, 3-methacryloxypropyltris(trimethylsiloxy)

silane, isobutyl methacrylate, itaconic acid, vinyl acetate, vinyl stearate, N,N-dimethylacrylamide, tert-butyl acrylamide, acrylonitrile, isobutyl vinyl ether, vinyl pyrrolidinone, vinyl azlactone, glycidyl methacrylate, 2-isocyanatoethyl methacrylate, maleic anhydride, vinyl triethoxysilane, vinyl tris(2-methoxyethoxy)silane, and 3-(trimethoxysilyl)propyl methacrylate. Polymers bearing hydrolyzable functionality are preferred. An acidic or basic catalyst may be used to accelerate the water cure of these compositions. Strong acid catalysts are preferred. A more complete description of suitable water reactive liquid organometallic compounds is disclosed in pending U.S. patent application Ser. Nos. 08/008,743 and 08/008,678.

Also included as presently more preferred resins in the instant invention are the water curable alkoxy silane terminated oligomers disclosed in copending U.S. Patent Application "Novel Casting Tapes and Resins and Processes Therefor," Ser. No. 08/048,656. These resin compositions are preferably solventless.

Preferred resin compositions are stable, i.e., nonreactive, and do not significantly increase in viscosity at a temperature of less than about 40° C. In addition, preferred resin compositions are capable of curing upon exposure to water to form a hardened material at a temperature between about 10° to 100 °C., preferably at a temperature between about 20° to 50° C. Preferred resin compositions include a low viscosity water-reactive alkoxysilane terminated polymer. The average alkoxysilane functionality is at least one and preferably at least two but may be as high as four. Each alkoxysilane group may have 2 or 3 hydrolyzable groups.

The water-reactive polymer having hydrolyzable terminal alkoxysilane groups is preferably a compound of the formula:

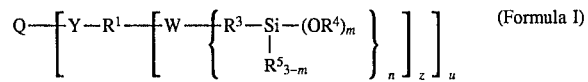    (Formula I)

wherein:

Q is a polyol residue;

W is —NHC(O)—X($R^2_{2-n-q}$)— or —XC(O)NH—;

X=—O—, —N—, or —S—;

Y is —O—, —N—, —S—, carbamylthio (—SC(O)NH—), carbamate (—OC(O)NH), or ureido, and N-substituted ureido (—NHC(O)NH—);

$R^1$ is a substituted or unsubstituted divalent bridging $C_1$–$C_{100}$ hydrocarbon group, optionally interrupted in the backbone by 1 to 50 nonperoxide —O—, —C(O)—, —S—, —SO$_2$—, —NR$^6$—, amide (—C(O)—NH—), ureido (—NH—C(O)—NH—), carbamate (—O—C(O)NH—), carbamylthio (—S—C(O)—NH—), unsubstituted or N-substituted allophanate (—NH—C(O)— N(C(O)—O—)—), unsubstituted and N-substituted biuret (—NH—C(O)—N(C(O)—N—)—), and N-substituted isocyanurate groups;

$R^2$ can be present (if n=1) or absent (if n=2) and is selected from the group consisting of a H and a substituted or unsubstituted $C_1$–$C_{20}$ hydrocarbon group, optionally interrupted in the backbone by 1 to 10 nonperoxide —O—, —C(O)—, —S—, —SO$_2$—, or —N(R$^6$)— groups;

$R^3$ is a substituted or unsubstituted divalent bridging $C_1$–$C_{20}$ hydrocarbon group, optionally interrupted in the backbone by 1 to 5 nonperoxide —O—, —C(O)—, —S—, —SO$_2$—, or —N(R$^6$)— groups;

$R^4$ is a $C_1$ to $C_6$ hydrocarbon group or —N=C(R$^7$)$_2$;

each $R^5$ and $R^7$ is independently a $C_1$ to $C_6$ hydrocarbon group;

$R^6$ is a $C_1$ to $C_6$ hydrocarbon group, or hydrogen;

n=1 to 2 and q=0 to 1, with the proviso that when X is N, n+q=1, and when X is S or O, n+q=2;

u=the functionality of the polyol residue=0 to 6, with the proviso that when u =0, the compound of Formula I is

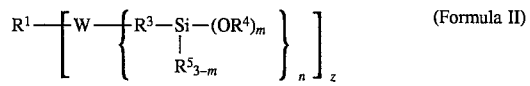    (Formula II)

m=2 to 3; and z=1 to 3.

Each "$R^3$–Si(OR$^4$)$_m$" moiety can be the same or different. A preferred composition consists of toluene diisocyanate ("TDI") based pre-polymers end-capped with highly functionalized alkoxy silanes, such as bis(trimethoxysilylpropyl)amine.

The currently preferred prepolymers are those formed from polyols and reactive polyisocyanates with free NCO ranging from 1.9 to 9.0 percent and contain polypropylene glycol, polytetramethylene glycol, and/or polyester ether polyols. The most preferred diisocyanate prepolymers are those containing polyethylene glycol, but include polyether polyols such as polytetramethylene glycol, polypropylene glycols, polybutylene glycols, and random or block copolymers of these, and polymer polyols such as those disclosed in U.S. patent application Ser. No. 07/376,421. Polyolefin polyols such as polybutadiene polyols and polyisoprene polyols may also be used as well as aromatic and aliphatic amine terminated "polyols" such as Jeffamine and Polamine materials, low molecular weight diols, thiols and the like. Mixtures and blends of these polyols may be useful. The preferred average polyol functionality is 1.8 to 3, more preferably 2 to 2.5 but polyols with functionalities as high as 4 or more may be useful.

The preferred polyisocyanates have differential reactivity, i.e. have at least one isocyanate group which is significantly more reactive than one or more isocyanate groups on the same molecule by a factor of 2 or more. The preferred isocyanates have a functionality of 2 to 3 while particularly preferred materials have functionalities of 2 to 2.3. The presently preferred isocyanate is TDI. Other aromatic isocyanates such as methylene diisocyanate ("MDI") and polyisocyanates based on condensation products of formaldehyde and aniline are potentially useful. Aliphatic isocyanates are useful and may be particularly preferred. for applications where stability to ultraviolet light is of particular concern. Materials such as the trimer and biuret adducts of hexamethylene isocyanate ("HMDI"), methylene-bis-(4-cyclohexylisocyanate), tetramethylxylene isocyanate ("TMXDI"), and xylene isocyanate could be used. Materials such as isophorone diisocyanate and the like are perhaps useful due to the differential reactivity of the isocyanate groups.

The preferred reactive silane of the present invention is bis(trimethoxysilylpropyl)amine, but other reactive silanes could be employed such as aminopropyltrimethoxysilane ("A-1110"), N-beta-(aminoethyl)-gamma -aminopropyl-trimethoxysilane ("A-1120"), gamma-mercaptopropyltrimethoxysilane ("Y-11167"), isocyanatopropyl trimethoxysilane, etc. Note that critical elements for a silane useful in the present invention are that it have:

at least one active hydrogen group (except when W=—XC(O)NH—);

at least one silane functionality; and at least 2 (and preferably 3) hydrolyzable groups in the silane(s).

Preferred silanes are trimethoxy- and triethoxy silanes but other trialkoxy, alkyldialkoxy, aryldialkoxy, and oximino silanes could be useful. These could also be reacted in various combinations and proportions with the TDI-based prepolymers to produce a wide range of average silane functionality (e.g., 2 to 4 or more).

Another important ingredient in the resins is the catalyst for the moisture curable resin. It has been found that substituted guanidines and particularly N,N,N',N'-tetramethylguanidine ("TMG") is the preferred catalyst for these silane cure systems ensuring a sufficiently rapid hydrolysis of the alkoxysilane groups and subsequent condensation of the resulting silanols to form siloxane adducts. However, other basic tertiary amine catalysts could be used in this resin system such as 1,8-diazobicyclo [5,4,0]undecan-7-one ("DBU"), triethylamine, imidazoles, piperazines, etc. Acid catalysts such as sulfonic acids (including alkyl and perfluoroalkyl), carboxylic acids (including alkyl and perfluoroalkyl), phosphoric acids, boric acids and the like could also be employed with this resin system. Moreover, various metal catalysts such as ligands of tin, cobalt, bismuth, lead, zinc or titanium which are known to the art of silane cure could be used alone or in combination with the aforementioned catalysts in this resin system.

The casting tapes of the present invention may comprise fillers such as described in co-pending U.S. Patent Application, filed concurrently with this application and by the assignee of this invention, entitled: "Novel Casting Materials," Ser. No. 08/099,007. As described in that application the curable resin may be mixed with a suitable filler to form a cohesive, and preferably porous, composite tape. Such composite tapes may further comprise a light weight fabric scrim to further enhance its cohesiveness.

Alternatively, the casting tape may comprise a scrim or fibrous sheet material upon which the curable resin can be coated. The sheet is preferably apertured such that the sheet is only partially impregnated with the resin. Examples of suitable sheets are non-woven, woven, or knit fabrics comprised of natural or synthetic fibers or materials. The sheet may alternatively be referred to as the "scrim" or the "backing."

Where fiberglass backings are desired, suitable sheets which may be employed are knit fiberglass fabrics such as disclosed in U.S. Pat. Nos. 4,502,479; 4,609,578; 4,668,563; and 5,014,403 and in U.S. patent application Ser. No. 07/976,402. Particularly preferred sheets of this type are extensible, heat-set fabrics as disclosed in U.S. Pat. No. 4,609,578 (Reed) which is herein incorporated by reference for its disclosure of suitable scrims. One example of a knitted fiberglass scrim which is within the scope of U.S. Pat. No. 4,609,578 is known by 3M, St. Paul, Minn., as the Scotchcast™ 2 knitted fiberglass scrim. The Scotchcast™ 2 scrim is used in the manufacture of 3M's Scotchcast™ 2 and Scotchcast™ Plus orthopedic casting materials.

Suitable non-fiberglass backings of the present invention include fabrics comprising: natural organic fibers; animal derived materials; naturally based organic polymer fibers; and synthetic polymer fibers. Suitable natural organic fibers for use in the fabric of the present invention include: acetate, azlon, rayon, and triacetate; and vegetable derived materials such as abaca, cotton, flax, hemp, jute, kapok, linen, ramie, and sisal. Suitable animal derived materials include wool, mohair, vicuna, other animal hairs, and silk. Presently preferred organic fibers include: cotton and wool. Cotton and rayon are presently most preferred.

Suitable synthetically prepared organic polymers include: acrylic, aramid, nylon, olefin (e.g., poly(1-butene), polyethylene, poly(3-methyl-1-butene), poly(1-pentene), polypropylene, and polystyrene), polyester, polytetrafluoroethylene, poly(vinyl alcohol), poly(vinyl chloride), and poly(vinylidine chloride). Presently preferred synthetic polymer fibers include: acrylic, nylon, polyethylene, polypropylene, and polyester. Presently most preferred synthetic polymer fibers include: nylon, and polyester. In this regard, preferred knitted, woven, or non-woven sheets made of organic fibers are described, for example, in U.S. Pat. Nos. 4,940,047; 4,984,566; and 4,841,958 (Ersfeld et al.) which are herein incorporated by reference.

The following examples are offered to aid in understanding of the present invention and are not to be construed as limiting the scope thereof. Unless otherwise indicated, all parts and percentages are by weight.

EXAMPLES

Example 1

PVA Film Liner Used to Provide Lubrication

In a dry environment (less than 4% relative humidity) a roll of commercially available 7.62 cm wide Scotchcast®2 casting tape (available from 3M Company, St. Paul, Minn.) was removed from its pouch, unwound from its core and rewound incorporating a water soluble liner between the layers. The liner was a poly(vinyl alcohol) ("PVA") liner commercially available as Aicello Solublon PVA film SA grade 17 micron thick (available from Mitsui Plastics Inc.—White Plains, N.Y.). The liner was supplied slit to a 7.62 cm width and was dried in an oven for 20 hours at 120° C. prior to use. The drying process made the film quite brittle but as long as no excessive tension was applied it was incorporated without breaking. The roll of casting tape with liner was sealed in an aluminum foil polyethylene laminate pouch until use.

The roll was removed from the pouch, immersed in ambient temperature water and squeezed three times while under water. The roll was removed and squeezed an additional time to remove excess water. The roll was applied to a 5.08 cm diameter mandrel. Small remains of the liner were present at the beginning of the roll but were not apparent further into the roll. The roll unwound much easier than a commercially available roll of Scotchcast 2. Furthermore, the tape was slippery during application and molding. The cast could be rubbed over its entire surface without sticking to the applier's hands and yet the curing and cured layers stuck together well.

Example 2

PVA Liner to Facilitate Removal of the Roll From the Package

A commercially available roll of 7.62 cm Scotchcast® Plus casting tape (available from 3M Company, St. Paul, Minn.) was removed from the pouch and a layer of PVA film prepared as described in Example 1 was applied around its circumference. The roll was placed back into a pouch and stored for several days. The roll was then removed from the pouch in the normal manner and was found to simply fall out without sticking to the inner surfaces of the pouch. The roll was dipped in water as described in Example 1, and the PVA film liner dissolved and the tape cured and hardened normally.

Example 3

PVA Liner Use to Prevent Transfer of Printed Colored Resin

Commercially available rolls of Scotchcast Plus were unrolled in a dry environment (less than 4% relative humidity) and a polka dot pattern was applied. The pattern was applied using a mixture of 50 parts Reactint Dark Blue 8119 reactive dye (Millikan Research Corp., Inman, S.C.) and 50 parts dibutyl phthalate. The dye and plasticizer mixture was applied to the resin coated tape using an open cell polyurethane foam sponge applicator by soaking the applicator with the colorant and then hand applying the spots of colorant. Two rolls were decorated and wound up as described in Example 1 with commercially available PVA films. The first roll was wound up using Aicello Solublon PVA film KBN 40 micron thick (available from Mitsui Plastics Inc.—White Plains, N.Y.). The second roll was wound up using a similar film having a 50 micron thickness. The rolls were stored with the length of the cylindrical roll lying horizontal for several days in a sealed aluminum foil—polyethylene laminate pouch.

The rolls were evaluated in the same manner described in Example 1. The film dissolved quickly and the polka dot pattern remained on the tape without layer to layer transfer. In addition, the PVA provided a creamy feel to the product.

Example 4

PVA Liner Used to Transfer a Printed Design to a Casting Tape

Magenta SD-MG2484 silk screen ink (comprising a pigment and binder in a hydrocarbon solvent) available from Radiant Color, Gardena, Calif. was applied in a polka dot pattern to the surface of the dried PVA liner described in Example 1. The pattern was applied using an open cell polyurethane foam as described in Example 3. The ink was allowed to dry and the printed liner was rolled up into a roll of Scotchcast 2 Casting Tape as described in Example 1 and sealed in an aluminum foil pouch.

The procedure was repeated using Reactint Maroon #846 (available from Millikan Research Corp., Inman, S.C.) as the colorant. The dye was applied using a rubber stamp with a raised letter "S". Some smearing of the image occurred when rolling up the liner/casting tape since the dye was not "fixed" in a binder as was the pigment described above.

Both products were evaluated using the procedure of curing the casting tape described in Example 1. The ink polka dot pattern transferred to the tape nicely, while the Reactint dye tended to smear. In this specific Example, the printed ink was more desirable than the dye.

Example 5

Rate of Dissolution of Various Water-Soluble Films

The time required to "dissolve" a water soluble film is characterized in accordance with the following test method. A single layer of film is cut and secured between the top and bottom halves of a Millipore Filter Holder (Part #4 but without its standard filter screen—Millipore Corp., Bedford, Mass.) to provide a 3.5 cm diameter piece of film secured in place. Twenty milliliters of water is gently added to the top of the fixture (creating approximately a 2 cm head atop the film) by pouring the water down the side of the fixture. The time for the water to dissolve the film and "break-through" the film (i.e., flow through the film) is recorded. Dissolution time is recorded as the mean break-through time of ten samples and is reported below in Table 5a.

TABLE 5a

| Run | Film | Thickness (micron) | Dissolution time (sec.) Undried film | Dissolution time (sec.) Dried film[4] |
|---|---|---|---|---|
| 1 | QSA 2004[1] | 38 | 12.5 | 24.9 |
| 2 | QSA 2004 | 51 | 23.5 | 50.3 |
| 3 | QSA 2000[1] | 38 | 21.3 | 47.2 |
| 4 | QSA 2000 | 51 | 37.0 | 96.1 |
| 5 | Aicello Solublon SA[2] | 17 | 2.7 | 3.7 |
| 6 | EM1100[3] | 53 | 22.3 | 49.9 |

[1] Available from Glenn Corp., St. Paul, Minn.
[2] Available from Mitsui Plastics Inc., White Plains, NY.
[3] Hydroxypropylmethylcellulose (CAS No. 009004-65-3) available from Glenn Corp., St. Paul, Minn.
[4] Dried for 20–24 hours at 100° C.

The above test yields a good approximation of the time required for dissolution of a film. However, as an alternative embodiment of the present invention one may choose to forego use of a separate film of liner and instead directly laminate the casting material with a water-soluble liner material. This liner film may be difficult, if not impossible, to later separate from the casting material and test in accordance with the above method. To test these liner materials it is acceptable to either employ a functional test (i.e., directly measure the casting tape under conditions of use and measure the time required for the liner to provide a lubricating effect) or a modification of the above "break-through" test. For example, one may directly form the liner film against the bottom surface of the Millipore filter (with the same thickness as found on the casting material) and then conduct the break-through test. Alternatively, one may form the liner film against the bottom surface of any other suitable porous substrate and place the laminate in the Millipore apparatus for testing as described above.

What is claimed is:

1. A method of enclosing a body member, with an orthopedic casting material comprising the steps of:

providing an orthopedic casting tape comprising a fabric sheet, a curable resin coated on said sheet, and a water soluble liner, wherein said curable resin-coated sheet is in the form of a wound roll configuration and said water soluble liner contacts said resin-coated sheet and separates the adjacent layers of the sheet when the sheet is in its wound configuration, said casting tape being pliable and formable prior to being cured and at least semi-rigid and strong after being cured;

initiating curing of said orthopedic casting tape and effectively dissolving said water soluble liner by contacting said casting tape with water wrapping the casting tape about the body member; and molding the wrapped casting tape about the body member.

2. A method of enclosing a body member according to claim 1, wherein said water soluble liner effectively dissolves when exposed to water in less than 30 seconds.

3. A method of enclosing a body member according to claim 1, wherein said water soluble liner has a thickness of less than 60 μm.

4. A method of enclosing a body member according to claim 1, wherein said water soluble liner effectively dissolves when exposed to water in less than 60 seconds and wherein said curable resin is a water-curable resin comprising isocyanate-functional prepolymers.

5. A method of enclosing a body member according to claim 1, wherein said water soluble liner effectively dissolves when exposed to water in less than 60 seconds and wherein said curable resin is a water-curable resin selected from the group consisting of water reactive liquid organometallic compounds and alkoxy silane terminated oligomers.

6. A method of enclosing a body member according to claim 1, wherein said curable resin sheet is in the form of a roll and said water soluble liner covers the roll of curable resin sheet such that when said roll of curable resin sheet is placed inside an outer pouch the major surface of said roll does not contact said pouch.

7. A method of enclosing a body member according to claim 1, wherein said water soluble liner comprises a polymer selected from the group consisting of polyvinylalcohol, polyethylene oxide, polyacrylamides, polyacrylic acids, cellulose ether polymers, polyethyloxazolines, polyethylene oxides, copolymers of polyethylene oxide and polypropylene oxide, esters of polyethylene oxide, esters of polyethylene oxide and polypropylene oxide polymers, urethanes of polyethylene oxide, and urethanes of polyethylene oxide and polypropylene oxide polymers.

8. A method of enclosing a body member according to claim 1, wherein said water soluble liner covers at least one major surface of said resin-coated sheet.

9. A method of enclosing a body member according to claim 1, wherein said liner covers both major surfaces of said curable resin sheet when the sheet is in an unwound configuration.

10. A method of enclosing a body member according to claim 9, wherein said liner is sealed at one or more edges of said curable resin sheet.

11. A method of enclosing a body member according to claim 1, wherein said liner further incorporates a plasticizer.

12. A method of enclosing a body member according to claim 11, wherein said plasticizer is externally incorporated into the liner component.

13. A method of enclosing a body member according to claim 1, wherein said curable resin is water curable, and said article further comprises a scrim wherein said scrim comprises a fiber selected from the group consisting of: inorganic fibers; natural organic fibers; animal derived materials; naturally based organic polymer fibers; and synthetic polymer fibers.

14. A method of enclosing a body member according to claim 13, wherein said scrim is a fiberglass knit, and said water soluble liner comprises a polymer selected from the group consisting of polyvinylalcohol, polyethylene oxide, polyacrylamides, polyacrylic acids, cellulose ether polymers, polyethyloxazolines, polyethylene oxides, copolymers of polyethylene oxide and polypropylene oxide, esters of polyethylene oxide, esters of polyethylene oxide and polypropylene oxide polymers, urethanes of polyethylene oxide, and urethanes of polyethylene oxide and polypropylene oxide polymers.

15. A method of enclosing a body member according to claim 1, wherein said curable resin sheet is in the form of a roll and said water soluble liner is in the form of a sheet which partially covers the outer cylindrical surface of said roll.

16. A method of enclosing a body member according to claim 1, wherein said liner is a continuous film.

17. A method of enclosing a body member according to claim 1, wherein said liner is a non-continuous sheet.

18. A method of enclosing a body member according to claim 1, wherein said resin-coated sheet and liner exhibits reduced tack after contact with water.

19. A method of enclosing a body member according to claim 1, wherein the roll exhibits reduced resin pooling during storage.

\* \* \* \* \*

UNITED STATES PATENT AND TRADEMARK OFFICE
CERTIFICATE OF CORRECTION

PATENT NO.:   5,603,691
DATED:        February 18, 1997
INVENTOR(S):  Matthew T. Scholz, Mark A. Berman, Dennis G. Bartizal and Michael D. Delmore It is certified that error appears in the above-identified patent and that said Letters Patent is hereby corrected as shown below:

Col. 1, line 14, "Pads" should read -- Paris --.

Col. 1, line 21, "Pads" should read -- Paris --.

Col. 1, line 23, "Pads" should read -- Paris --.

Col. 2, line 53, "08/045,007" should read -- 08/049,007 --.

Col. 8, line 17, "Coming" should read -- Corning --.

Col. 8, line 18, "Coming" should read -- Corning --.

Col. 11, line 31, "08/099,007" should read -- 08/049,007 --.

Signed and Sealed this

Twenty-third Day of June, 1998

Attest:

BRUCE LEHMAN

Attesting Officer          Commissioner of Patents and Trademarks